United States Patent [19]

Iizuka et al.

[11] 4,320,134

[45] Mar. 16, 1982

[54] INHIBITON OF THROMBOXANE SYNTHETASE WITH 1-SUBSTITUTED IMIDAZOLE COMPOUNDS

[75] Inventors: Kinji Iizuka; Kenji Akahane; Yukio Kamijo; Denichi Momose, all of Matsumoto; Yukiyoshi Ajisawa, Okaya, all of Japan

[73] Assignees: Ono Pharmaceutical Co., Ltd., Osaka; Kissei Pharmaceutical Co., Ltd., Matsumoto, both of Japan

[21] Appl. No.: 14,001

[22] Filed: Feb. 21, 1979

[30] Foreign Application Priority Data

Feb. 18, 1978 [JP] Japan .................................. 53-18054
Feb. 20, 1978 [JP] Japan .................................. 53-18340

[51] Int. Cl.$^3$ .................. A61K 31/415; C07D 233/60
[52] U.S. Cl. ........................... 424/273 R; 548/341
[58] Field of Search .................. 548/341; 424/273 R

[56] References Cited

U.S. PATENT DOCUMENTS

3,531,494 9/1970 Adolphi et al. ..................... 548/341
3,767,602 10/1973 Carroll et al. ...................... 521/118
3,912,689 10/1975 Bechara et al. ..................... 548/341

FOREIGN PATENT DOCUMENTS

2638470 3/1977 Fed. Rep. of Germany ...... 548/341
40-8544 5/1965 Japan ................................. 548/341

OTHER PUBLICATIONS

Bayer, Chem. Abst., 1966, vol. 64, columns 11215-11216.
Pailer et al., Monatshefte for Chemie, 1977, vol. 108, pp. 1059-1066.
Rahman et al., Chem. Abst., 1975, vol. 83, No. 164069u.
Schwan, Chem. Abst., 1968, vol. 68, No. 39536h.
Staab et al., Chem. Abst., 1962, vol. 57, columns 5906-5907.
Tanaka et al., Chem. Abst., 1977, vol. 87, No. 200849s.
Yamauchi et al., Chem. Abst., 1976, vol. 84, No. 121785c.
Moncada, S. et al., *Prostaglandins*, 13(4), 611-629 (1977).
Hamberg, M. et al., *Proc. Nat. Acad. Sci., USA*, 72(8), 2994-2998 (1975).
Needleman, P. et al., *Nature*, 261, 558-560 (1976).

*Primary Examiner*—Richard A. Schwartz
*Attorney, Agent, or Firm*—Sughrue, Mion, Zinn, Macpeak and Seas

[57] ABSTRACT

The imidazole compounds of the general formula (I):

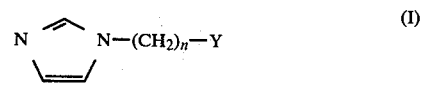

(I)

wherein Y is a carboxyl group, a hydroxymethyl group, an N-di or -mono alkyl substituted or unsubstituted carbamoyl group, a cyano group, or an N-di or -mono alkyl substituted or unsubstituted aminomethyl group, and n is an integer of 3 to 20; and pharmaceutically acceptable salts thereof. These compounds have a strong inhibitory effect on thromboxane synthetase from rabbit platelet microsomes, and are useful as therapeutically active agents for inflammation, hypertension, thrombus, cerebral apoplexy and asthma.

14 Claims, No Drawings

INHIBITON OF THROMBOXANE SYNTHETASE WITH 1-SUBSTITUTED IMIDAZOLE COMPOUNDS

BACKGROUND OF THE INVENTION

1. Field of the Invention

This invention relates to novel imidazole compounds. More particularly, this invention relates to N-(ω-substituted alkyl)imidazole compounds possessing an extremely strong inhibitory action for thromboxane synthetase and inhibiting the biosynthesis of thromboxane $A_2$.

2. Description of the Prior Art

Up to now, of the compounds having an imidazole skeleton, it has been reported that imidazole and 1-methylimidazole possess and inhibitory action for thromboxane synthetase (Prostaglandins, Vol. 13, No. 4, 611–, 1977). However, since their inhibitory action for thromboxane synthetase is weak, these compounds are hardly applicable as practically effective medicines. Therefore, research directed towards developing compounds possessing a much stronger and more specific inhibitory effect on thromboxane synthetase has been long conducted in this field.

On the other hand, N-(6-methoxycarbonylhexyl)-imidazole has already been synthesized by P. Matthias et al and is publicly known (Monatsch Chem., Vol. 108, No. 5, 1059–, 1977). Although that compound tends to have a stronger inhibitory effect on thromboxane synthetase when compared with imidazole or 1-methylimidazole, the inhibitory effect is not completely satisfactory as a practical medication.

The compounds of this invention possess a strong and specific inhibitory action for thromboxane synthetase, and are useful as therapeutically active agents for inflammation, hypertension, thrombus, cerebral apoplexy and asthma.

SUMMARY OF THE INVENTION

Accordingly, a principal object of this invention is to provide compounds which exhibit a strong and specific inhibitory effect on thromboxane synthetase, and which are therapeutically useful.

Another object of this invention is to provide new and pharmacologically effective imidazole compounds.

Still another object of this invention is to provide N-(ω-substituted alkyl)imidazole compounds and pharmaceutically acceptable salts thereof.

Other objects, features and advantages of this invention will become more apparent from the following description of the invention.

DETAILED DESCRIPTION OF THE INVENTION

Accordingly, the present invention provides imidazole compounds of the general formula (I)

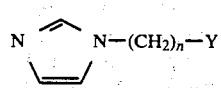

(I)

wherein Y is a carboxyl group, a hydroxymethyl group, an N-di or -mono alkyl substituted or unsubstituted carbamoyl group, a cyano group or an N-di or -mono alkyl substituted or unsubstituted aminomethyl group, and n is an integer of 3 to 20, and pharmaceutically acceptable salts thereof.

The term "alkyl" as used herein means a straight or branched chain alkyl group having 1 to 4 carbon atoms.

The term "alkoxy" as used herein means an alkoxy group having 1 to 4 carbon atoms.

The term "acyloxy" as used herein means an acyloxy group derived from an aliphatic carboxylic acid having 2 to 5 carbon atoms.

The imidazole compounds of the general formula (I) of this invention exhibit an inhibitory action for thromboxane synthetase from rabbit platelet microsomes. That is, the imidazole compounds of this invention inhibit conversion of PROSTAGLANDIN $H_2$ into THROMBOXANE $B_2$ via THROMBOXANE $A_2$ which is an unstable intermediate, and which is known to induce irreversible platelet aggregation and to contract smooth muscle and particularly muscle of blood vessel. (Nature, Vol. 261, No. 6, 17–, 1976). These results demonstrate that the imidazole compounds of this invention inhibit the biosynthesis of thromboxane $A_2$, and are thus useful for treatment of diseases caused by thromboxane $A_2$, such as inflammation, hypertension, thrombus, cerebral apoplexy and asthma.

The inhibitory action of the imidazole compounds of this invention can be confirmed by determination of the thromboxane $B_2$ produced by thromboxane synthetase from prostaglandin $H_2$ via thromboxane $A_2$. Furthermore, the inhibitory action of the imidazole compounds of this invention can be confirmed by determination of the inhibitory effect on platelet aggregation caused by arachidonic acid (arachidonic acid is converted to prostaglandin $H_2$ by cyclooxygenase, and prostaglandin $H_2$ is converted to thromboxane $B_2$ via thromboxane $A_2$ which is known to induce platelet aggregation as described above). Further still, the inhibitory action of the imidazole compounds of this invention can be confirmed by determination of the inhibitory effect on sudden deaths caused by arachidonic acid.

The imidazole compounds of this invention are characterized by the presence of an alkylene chain as an N-substituent of the imidazole skeleton, which consists of 3 to 20 carbon atoms and which has a functional group at the ω-position of the alkylene chain, selected from the group consisting of a carboxy group, a hydroxymethyl group, an N-di or -mono alkyl substituted or unsubstituted carbamoyl group, a cyano group and an N-di or -mono alkyl substituted or unsubstituted aminomethyl group.

In the present invention, the alkylene chain is limited to a straight saturated alkylene chain having 3 to 20 carbon atoms.

In the imidazole compounds of this invention, the carbon number of alkylene chain and the species of the functional groups at the ω-position of alkylene chain play an important role in providing the inhibitory effect. That is, in general, the potency of the inhibitory action for thromboxane synthetase becomes higher as the carbon number of alkylene chain increases. Suitable alkylenes are pentamethylene, heptamethylene, octamethylene, nonamethylene, decamethylene and undecamethylene chains.

On the other hand, a carboxyl group, a hydroxymethyl group, an N-di or -mono alkyl substituted or unsubstituted carbamoyl group, a cyano group and an N-di or -mono alkyl substituted or unsubstituted aminomethyl group can be employed in this invention as the functional group at the ω-position of alkylene chain. Of the functional groups at the ω-position of alkylene chain, a carboxyl group, a hydroxymethyl group, an N-di or -mono alkyl substituted or unsubstituted carbamoyl group and a cyano group are preferred. In this invention, a carboxyl group is the more preferred functional group at the ω-position of the alkylene chain.

However, compounds substituted with an alkoxycarbonyl group or a methyl group at the ω-position of the alkylene chain, i.e., N-(ω-lower alkoxycarbonyl alkyl)-imidazoles or N-alkylimidazoles, possess a significantly weaker inhibitory effect in comparison to the corresponding carboxylic acid compounds of the general formula (I) of this invention.

Preferred examples of the imidazole compounds of this invention include compounds wherein n is an integer of 5 to 11 and Y is a carboxyl group in the general formula (I). That is, 1-(5-carboxypentyl) imidazole, 1-(6-carboxyhexyl)imidazole, 1-(7-carboxyheptyl) imidazole, 1-(8-carboxyoctyl)imidazole, 1-(9-carboxynonyl)imidazole, 1-(10-carboxydecyl)imidazole, 1-(11-carboxyundecyl)imidazole. are preferred. More preferred examples of the imidazole compounds of this invention include the compounds wherein n is an integer of 6 to 9 and Y is a carboxyl group in the general formula (I). 1-(6-carboxyhexyl)imidazole, 1-(7-carboxyheptyl)imidazole, 1-(8-carboxyoctyl)imidazole and 1-(9-carboxynonyl)imidazole are more preferred.

The imidazole compounds of the general formula (I) of this invention can be prepared by the following procedures.

Of the imidazole compounds of the general formula (I), for example, the compounds of the general formula (Ia):

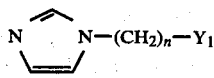
(Ia)

wherein $Y_1$ is a carboxyl group, a hydroxymethyl group, an N-di or -mono alkyl substituted or unsubstituted carbamoyl group or a cyano group, and n is an integer of 3 to 20, can be prepared by reacting imidazole of the formula (II):

(II)

with a compound of the general formula (III):

   (III)

wherein X is an acid residual group, W is a carboxyl group, an alkoxycarbonyl group, a cyano group, an acyloxymethyl group or an N-di or -mono alkyl substituted or unsubstituted carbamoyl group, and n has the same meaning as given above; and then optionally hydrolyzing the resulting product when W represents an alkoxycarbonyl group or an acyloxymethyl group.

On the other hand, of the imidazole compounds of the general formula (I), the compounds of the general formula (Ib):

(Ib)

wherein $Y_2$ is an N-di or -mono alkyl substituted or unsubstituted aminomethyl group and n is the same as defined above, can be prepared by reacting imidazole of the formula (II):

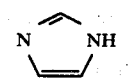
(II)

with a compound of the general formula (III'):

   (III')

wherein $W_1$ is a cyano group, or an N-di or -mono alkyl substituted or unsubstituted carbamoyl group, and X and n have the same meanings as given above, to produce a compound of the general formula (Ic):

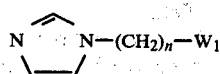
(Ic)

wherein $W_1$ and n have the same meaning as given above, then hydrogenating the resulting compound and, optionally, reacting the resulting compound with an alkyl halide to introduce the desired N-alkyl group.

The N-alkylation described above in the reaction of imidazole of the formula (II) with a compound of the general formula (III) or (III') can be carried out according to well known methods. That is, imidazole is dissolved in an inert organic solvent, e.g., benzene, tetrahydrofuran, dioxane, toluene, xylene, acetonitrile, N,N-dimethylformamide, ethanol, butanol, etc. Then a basic substance such as sodium carbonate, potassium carbonate, sodium hydroxide, potassium hydroxide, sodium alkoxide, diisopropylethylamine, pyridine, triethylamine, etc., in an equimolar amount to imidazole, is added to the solution, and the mixture is heated to about 20° to about 150° C., preferably about 60° to 100° C., for about 10 minutes to about 2 hours, preferably about 30 minutes to 1 hour. Subsequently, the compound of the general formula (III) or (III') in a proportion of about 1 to 0.9 mol per mol of imidazole is added to the reaction mixture, the reaction mixture is heated to about 50° to about 150° C., preferably about 60° to 120° C.,for about 10 minutes to 5 hours, preferably about 2 hours to 3 hours, and then the reaction product is concentrated under reduced pressure, the residue is recrystallized or distilled to obtain the desired product. If desired, the resulting product is hydrolyzed in an aqueous solution of an acid or an alkali to obtain the desired product.

In this process, instead of using the basic substance, the reaction may be carried out by using imidazole in an excess amount, e.g., more than twice the molar amount of the compound of the general formula (III) or (III') above. The reaction can also be carried out in the absence of any solvent.

Furthermore, the above reaction can be carried out by reacting the compound of the general formula (III) or (III') with a silver salt of the imidazole instead of the imidazole. The silver salt may be formed by reacting imidazole with a silver salt such as silver nitrate, etc. The reaction can also be carried out in the presence of a crown ether or a phase transfer catalyst such as tetrabutyl ammonium bromide, etc.

The above-mentioned hydrogenation of the compound of the general formula (Ic) can also be carried out according to well known methods. That is, the compound of the general formula (Ic) may be dissolved in an inert organic solvent, e.g., diethyl ether, tetrahydrofuran, benzene, toluene, xylene, etc., and an adequate amount of hydrogenating agent such as lithium aluminium hydride, etc., is added to the solution, the mixture is stirred at room temperature or heated to about 30° to about 100° C., preferably about 50° to 100° C., for about 3 to 10 hours, preferably about 5 to 8 hours. Then, the reaction mixture is treated in the usual manner and the desired product can be obtained by recrystallization or distillation.

In this process, the compound wherein $W_1$ is a cyano group in the general formula (Ic) can also be converted to the desired product by catalytic hydrogenation in the presence of a catalyst such as palladium-charcoal, platinum dioxide, etc., under a hydrogen gas-atmosphere.

In the process of this invention, the imidazole used as starting material is well known and can easily be prepared according to methods disclosed in the literature. The compounds of the general formula (III) and (III') are also known compounds and can also easily be prepared according to methods disclosed in the literature. In the compounds of the general formula (III) and (III'), halogen atoms and acid residual groups formed from organic sulfonic acids, i.e., arylsulfonyloxy and alkylsulfonyloxy groups, can be employed in the process of this invention as acid residual groups.

In this invention, examples of the compounds of the general formula (III) or (III') inclue straight chain saturated alkylenes having 3 to 20 carbon atoms, which have a functional group selected from a carboxyl group, an alkoxycarbonyl group, an acyloxymethyl group, an N-di or -mono alkyl substituted or unsubstituted carbamoyl group and a cyano group at the 1-position of alkylene, and which have an acid residual group at the ω-position on the opposite end of the alkylene chain. Preferred examples of these compounds include 6-bromohexanoic acid, 7-bromoheptanoic acid, 8-bromooctanoic acid, 9-bromononanoic acid, 10-bromodecanoic acid, 11-bromoundecanoic acid, 12-bromododecanoic acid and alkyl esters of these acids, 6-bromohexanenitrile, 7-bromoheptanenitrile, 8-bromooctanenitrile, 9-bromononanenitrile, 10-bromodecanenitrile, 11-bromoundecanenitrile, 12-bromododecanenitrile, 6-bromohexaneamide, 7-bromoheptaneamide, 8-bromooctaneamide, 9-bromononaneamide, 10-bromodecaneamide, 11-bromoundecaneamide, 12-bromododecaneamide and N-di or -mono alkyl substituted amides of these amides, 1-acetoxy-6-bromohexane, 1-acetoxy-7-bromoheptane, 1-acetoxy-8-bromooctane, 1-acetoxy-9-bromononane, 1-acetoxy-10-bromodecane, 1-acetoxy-11-bromoundecane and the like.

The compounds of the general formula (I) of this invention having a free carboxyl group or a free amino group can be converted according to usual methods to pharmaceutically acceptable salts thereof. For example, the free-form compound of the general formula (I) is dissolved in solvent, e.g., an alcohol, water, etc., an adequate amount of hydrochloric acid or sodium hydroxide is added to the solution, the mixture is stirred at room temperature or warmed for an adequate period of time, the solvent is then distilled away, and the residue is recrystallized to obtain the salt of compound of the general formula (I). As examples of such pharmaceutically acceptable acid addition salts, in addition to the hydrochloric acid salt, there are the hydrobromic acid salt, the sulfuric acid salt, the nitric acid salt, the phosphoric acid salt, the sulfonic acid salt, the benzoic acid salt, the succinic acid salt, the tartaric acid salt, the citric acid salt, etc. On the other hand, as examples of such pharmaceutically acceptable base addition salts, in addition to the sodium salt, there are the potassium salt, the calcium salt, the magnesium salt, etc.

In the case of the salts of the compounds of the general formula (I), the salt form of the compounds can be converted by usual methods to the free form of the compound thereof. For example, the salt form of the compound of the general formula (I) is dissolved in water, then an adequate amount of hydrochloric acid or sodium hydroxide is added to the solution, and the mixture is stirred at room temperature for an adequate period of time, water is removed, and the residue is distilled under reduced pressure or recrystallized from an adequate solvent to obtain the desired compound.

Acid or base addition salts of the compounds of this invention have as high an inhibitory effect on thromboxane synthetase as the corresponding compounds having a free amino group or an acid group.

The imidazole compounds of this invention possess a strong inhibitory effect on thromboxane synthetase, and are useful as therapeutically active agents for inflammation, hypertension, thrombus, cerebral apoplexy and asthma.

The imidazole compounds of the general formula (I) and the pharmaceutically acceptable salts thereof of the present invention can be administered to mammals including humans by oral, intravenous, intramuscular or intrarectal administration, and for administration they can be formulated into pharmaceutical compositions together with conventional pharmaceutically acceptable carriers.

The compounds can be administered in various forms depending on the type of therapy. Typical dosage forms which can be used are tablets, pills, powders, liquid preparations, suspensions, emulsions, granules, capsules, suppositories and injectable preparations.

In molding the pharmaceutical composition into a tablet form, a wide variety of conventional carriers known in this art can be used. Examples of suitable carriers are excipients, such as glucose, lactose, starch, cacao butter, hardened vegetable oils, kaolin and talc, binders, such as gum arabic powder, tragacanth powder, and ethanol, and disintegrants, such as laminaria and agar. The tablets, if desired, can be coated and made into sugar-coated tablets, gelatin-coated tablets, enteric-coated tablets, film-coated tablets, or tablets coated with two or more layers.

When the pharmaceutical composition is formulated into an injectable preparation, the resulting solution and suspension are preferably sterilized, and are isotonic with respct to blood. In making the pharmaceutical composition into a solution or suspension, all diluents customarily used in the art employed. Examples of suitable diluents are water, ethyl alcohol, propylene glycol, ethoxylate isostearyl alcohol, polyoxyethylene sorbitol, and sorbitan esters. Sodium chloride, glucose or glycerol may be incorporated into a therapeutic agent in an amount sufficient to prepare an isotonic solution. The therapeutic agent may further contain ordinary dissolving aids, buffers, pain-alleviating agents, and preservatives, and optionally, coloring agents, perfurmes, flavors, sweeteners, and other drugs.

The dosage of the compound of this invention is about 1 mg to 1,000 mg/body oral, or about 0.1 mg to 100 mg/body injected per day in multiple doses depending upon the disease which is being treated.

This invention is further illustrated in more detail by way of the following examples wherein the melting point or the boiling point of the product obtained is uncorrected. Unless otherwise indicated, all parts, percents, ratios and the like are by weight.

EXAMPLE 1

1-(7-Carboxyheptyl)imidazole Hydrochloride

To a suspension of 4.6 g of sodium hydride (9.2 g of 50% sodium hydride was washed with petroleum ether to remove the mineral oil) in 400 ml of dry N,N-dimethylformamide was added 13 g of imidazole at room temperature and then the mixture was heated to 90° C.

A solution of 43 g of methyl 8-bromooctanoate in 50 ml of dry N,N-dimethylformamide was added to the mixture at 90° C. over a period of 1 hour, and then the reaction mixture was heated at 90° C. for 1 hour.

After concentration under reduced pressure, 500 ml of ether was added to the residual oil and washed with water and dried over magnesium sulfate.

The solvent was evaporated and the residual oil was distilled under vacuum (165°–170° C./1 mmHg) to give 32 g of 1-(7-methoxycarbonylheptyl)imidazole as a pale yellow oil.

IR Absorption Spectrum (neat)

$\nu$CH: 3100 cm$^{-1}$
$\nu$CO: 1730 cm$^{-1}$

NMR Spectrum (CDCl$_3$)

$\delta$1.1–2.0 (m, 10H), 2.29 (t, 2H), 3.64 (s, 3H), 3.92 (t, 2H), 6.87 (t, 1H), 6.98 (br-s, 1H), 7.40 (br-s, 1H)

Elemental Analysis

Calcd. for C$_{12}$H$_{20}$O$_2$N$_2$ (%): C, 64.25; H, 8.99; N, 12.49; Found (%): C, 64.12; H, 9.02; N, 14.37.

The ester (10.0 g) was then stirred with 2.3 g of sodium hydroxide in 30 ml of water at room temperature for 1 hour. After concentration under reduced pressure, an excess of 3 N hydrochloric acid was added to the residue and the acidic solution was concentrated under reduced pressure to remove the hydrochloric acid completely.

The residual solid was dissolved in ethanol and the insoluble salts were filtered off.

The filtrate was evaporated and the residual crystals were recrystallized from ethanol to give 8.7 g of 1-(7-carboxyheptyl)imidazole hydrochloride as colorless leaflets (m.p. 153°–154° C.).

IR Absorption Spectrum (KBr)

$\nu$CH: 3130 cm$^{-1}$
$\nu$CO: 1710 cm$^{-1}$

NMR Spectrum (DMSO-d$_6$)

$\delta$1.1–2.0 (m, 10H), 2.19 (t, 2H), 4.20 (t, 2H), 7.63 (t, 1H), 7.77 (t, 1H), 9.24 (br-s, 1H), 10-12 (br, 2H)

Elemental Analysis

Calcd. for C$_{11}$H$_{19}$O$_2$N$_2$Cl (%): C, 53.54; H, 7.76; N, 11.35; Found (%): C, 53.38; H, 7.96; N, 11.41.

The following compounds can be prepared in a similar manner.

| Starting Material | n | Reaction Condition | R | Z | Yield | b.p. | Reaction Condition | R | Z |
|---|---|---|---|---|---|---|---|---|---|
| Br(CH$_2$)$_4$CO$_2$Et | 4 | NaH/DMF 80° C. 2 hr. | Et | — | 78% | 149–150° C./1 mmHg colorless oil | (1) NaOH-aq. R.T. 15 min. (2) d. HCl | H | HCl |
| Br(CH$_2$)$_5$CO$_2$Et | 5 | NaH/DMF 90° C. 2 hr. | Et | — | 70% | 160–162° C./2 mmHg colorless oil | (1) NaOH-aq. R.T. 20 min. (2) d. HCl | H | HCl |
| TsO(CH$_2$)$_8$CO$_2$Me | 8 | NaH/DMF 90° C. 1 hr. | Me | — | 88% | not determined colorless oil | (1) NaOH-aq. 60° C. 1 hr. (2) d. HCl | H | HCl |
| Br(CH$_2$)$_9$CO$_2$Et | 9 | NaH/DMF 90° C. 2.5 hr. | Et | — | 75% | 175–181° C./1.5 mmHg colorless oil | (1) NaOH-aq. 60° C. 15 min. (2) 3N-HCl | H | HCl |
| Br(CH$_2$)$_6$CO$_2$Et | 6 | NaH/DMF 110° C. 1.5 hr. | Et | — | 67% | 142–145° C./1 mmHg colorless oil | (1) NaOH-aq. R.T. 15 min. (2) d. HCl | H | HCl |
| Br(CH$_2$)$_{10}$CO$_2$Me | 10 | NaH/DMF 100° C. 1 hr. | Me | — | 70% | 190–192° C./0.5 mmHg colorless oil | (1) NaOH-aq./MeOH (1:1) R.T. 30 min. (2) d. HCl | H | HCl |
| Br(CH$_2$)$_{11}$CO$_2$Et | 11 | NaH/DMF 90–100° C. 2 hr. | Et | — | 55% | 208–209° C./0.5 mmHg colorless oil | (1) NaOH-aq./MeOH (1:2) 70° C. 1 hr. (2) d. HCl | H | HCl |
| Br(CH$_2$)$_{16}$CO$_2$Me | 16 | NaH/DMF 90° C. 40 min. | Me | — | 64% | not determined pale yellow oil | (1) NaOH-aq./MeOH (1:2) reflux 2 hr. (2) d. HCl | H | HCl |
| Br(CH$_2$)$_3$CO$_2$Et | 3 | NaH/DMF 90° C. 1 hr. | Et | — | 72% | 108–112° C./0.5 mmHg colorless oil | (1) NaOH-aq. R.T. 15 min. (2) d. HCl | H | HCl |

EXAMPLE 2

1-(7-Carboxyheptyl)imidazole

A solution of 20.0 ml of 0.1 N sodium hydroxide (2.0 mmoles) was added to 493.5 mg (2.0 mmoles) of 1-(7-carboxyheptyl)imidazole hydrochloride, which was prepared by the same procedure as described in Example 1, and then the solution was concentrated under reduced pressure.

The residual solid was dissolved in ethanol and insoluble salts were filtered off.

The filtrate was evaporated under reduced pressure and the residual crystals were recrystallized from ethanolether to give 340 mg of 1-(7-carboxyheptyl)imidazole as colorless crystals (m.p.: 91°–94° C.).

IR Absorption Spectrum (KBr)

νCH: 3130 cm$^{-1}$
νCO: 1700 cm$^{-1}$

NMR Spectrum (CDCl$_3$)

δ1.0–2.0 (m, 10H), 2.30 (t, 2H), 3.92 (t, 2H), 6.85 (s, 1H), 7.03 (s, 1H), 7.62 (s, 1H), 11.80 (br-s, 1H)

Elemental Analysis

Calcd. for C$_{11}$H$_{18}$O$_2$N$_2$ (%): C, 62.83; H, 8.63; N, 13.32; Found (%): C, 62.55; H, 8.83; N, 13.10.

The following compounds can be prepared in a similar manner.

100° C. over a period of 30 minutes, and the reaction mixture was further heated at 100° C. for 30 minutes.

After evaporation of N,N-dimethylformamide under reduced pressure, the residual oil was heated in 40 ml of 10% sodium hydroxide at 70° C. for 30 minutes.

The solution was concentrated under reduced pressure and the residue was dissolved in dichloromethane. The insoluble solid was filtered off and dried over magnesium sulfate.

After removal of dichloromethane, the residual oil was distilled under vacuum (169°–170° C./0.5 mmHg) to give 12.0 g of 1-(6-hydroxyhexyl)imidazole as a colorless oil.

IR Absorption Spectrum (neat)

νOH: 3240 cm$^{-1}$
νCH: 3100 cm$^{-1}$

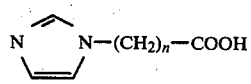

| n | m.p. | IR (KBr): cm$^{-1}$ | NMR (DMSO—d$_6$): δ |
|---|---|---|---|
| 3 | 134–135.5° C. (colorless prisms) | ν CH: 3140 ν CO: 1700 | 1.8–2.3 (m, 4H), 3.97 (t, 2H), 6.88 (s, 1H), 7.13 (s, 1H), 7.63 (s, 1H), 10.5 (br-s, 1H) |
| 4 | 165–166.5° C. (colorless needles) | ν CH: 3130 ν CO: 1705 | 1.3–1.9 (m, 4H), 2.24 (t, 2H), 3.96 (t, 2H), 6.86 (s, 1H), 7.10 (s, 1H), 7.60 (s, 1H), 8.15 (br, 1H) |
| 5 | 139–140° C. (colorless prisms) | ν CH: 3100 ν CO: 1700 | 1.0–1.9 (m, 6H), 2.20 (t, 2H), 3.95 (t, 2H), 6.85 (s, 1H), 7.12 (s, 1H), 7.60 (s, 1H), 9–10 (br, 1H) |
| 6 | 132–133° C. (colorless prisms) | ν CH: 3140 ν CO: 1705 | 1.1–1.8 (m, 8H), 2.17 (t, 2H), 3.92 (t, 2H), 6.84 (s, 1H), 7.10 (s, 1H), 7.58 (s, 1H), 9–10 (br, 1H) |
| 8 | 121–122° C. (colorless prisms) | ν CH: 3130 ν CO: 1700 | 1.0–1.8 (m, 12H), 2.18 (t, 2H), 3.93 (t, 2H), 6.85 (br-s, 1H), 7.10 (br-s, 1H), 7.59 (br-s, 1H) |
| 9 | 124–125° C. (colorless leaflets) | ν CH: 3140 ν CO: 1705 | 1.1–1.8 (m, 14H), 2.18 (t, 2H), 3.94 (t, 2H), 6.85 (br-s, 1H), 7.11 (br-s, 1H), 7.59 (br-s, 1H) |
| 10 | 126–127° C. (colorless needles) | ν CH: 3130 ν CO: 1700 | 1.1–1.8 (m, 16H), 2.18 (t, 2H), 3.95 (t, 2H), 6.85 (br-s, 1H), 7.11 (br-s, 1H), 7.58 (br-s, 1H) |
| 11 | 134–134.5° C. (colorless needles) | ν CH: 3140 ν CO: 1705 | 1.0–2.0 (m, 18H), 2.32 (t, 2H), 4.20 (t, 2H), 7.33 (br-s, 1H), 7.57 (br-s, 1H), 8.07 (br-s, 1H), 10.2–11.2 (br, 1H) |

EXAMPLE 3

1-(6-Hydroxyhexyl)imidazole

To a suspension of 4.8 g of 50% sodium hydride (dispersed in mineral oil) in 150 ml of dry N,N-dimethylformamide was added slowly 6.8 g of imidazole at room temperature.

The mixture was then heated to 100° C. and 22.5 g of 1-acetoxy-6-bromohexane was added to the mixture at NMR Spectrum (CDCl$_3$)

δ1.2–1.95 (m, 8H), 3.60 (t, 2H), 3.84 (s, 1H), 3.92 (t, 2H), 6.85 (t, 1H), 6.97 (br-s, 1H), 7.40 (s, 1H)

Elemental Analysis

Calcd. for C$_9$H$_{16}$ON$_2$ (%): C, 64.25; H, 9.59; N, 16.65; Found (%): C, 64.32; H, 9.39; N, 16.42.

The following compounds can be prepared in a similar manner.

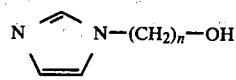

| n | b.p. | Yield (%) | IR (neat) cm$^{-1}$ | NMR (CDCl$_3$): δ |
|---|---|---|---|---|
| 4 | 135–138° C. (0.5 mmHg) | 70 | ν OH: 3230 ν CH: 3120 | 1.4–2.0 (m, 4H), 3.05 (br-s, 1H), 3.64 (t, 2H), 3.96 (t, 2H), 6.85 (t, 1H), 6.97 (t, 1H), 7.38 (s, 1H) |
| 5 | 175–178° C. (1 mmHg) | 65 | ν OH: 3240 ν CH: 3110 | 1.1–2.0 (m, 6H), 3.58 (t, 2H), 3.90 (t, 2H), 4.90 (br, 1H), 6.84 (t, 1H), 6.92 (t, 1H), 7.37 (s, 1H) |
| 7 | 159–162° C. | 68 | ν OH: 3250 | 1.15–1.90 (m, 10H), 3.17 (br-s, 1H), 3.62 (t, 2H), |

-continued $$N\underset{\diagdown=\diagup}{\overset{\diagup\frown\diagdown}{N}}N-(CH_2)_n-OH$$

| n | b.p. | Yield (%) | IR (neat) cm$^{-1}$ | NMR (CDCl$_3$): δ |
|---|---|---|---|---|
|  | (1 mmHg) |  | ν CH: 3100 | 3.91 (t, 2H), 6.85 (t, 1H), 6.98 (br-s, 1H), 7.40 (s, 1H) |
| 9 | — | 60 | ν OH: 3300 ν CH: 3120 |  |

EXAMPLE 4

1-(7-Cyanoheptyl)imidazole

A mixture of 6.8 g of imidazole, 16.0 g of 7-chloroheptanenitrile, and 20 g of anhydrous potassium carbonate in 250 ml of xylene was refluxed for 4.5 hours.

After cooling, the reaction mixture was filtered and evaporated under reduced pressure.

The residual oil was distilled under vacuum (192° to 194° C./1 mmHg) to give 12.5 g of 1-(7-cyanoheptyl)imidazole as a colorless oil.

IR Absorption Spectrum (neat)

νCH: 3100 cm$^{-1}$
νCN: 2240 cm$^{-1}$

NMR Spectrum (CDCl$_3$)

δ 1.2–2.0 (m, 10H), 2.32 (t, 2H), 3.92 (t, 2H), 6.85 (t, 1H), 7.00 (t, 1H), 7.40 (s, 1H)

Elemental Analysis

Calcd. for C$_{11}$H$_{17}$N$_3$ (%): C, 69.07; H, 8.96; N, 21.97; Found (%): C, 69.15; H, 8.95; N, 21.93.

The following compounds can be prepared in a similar manner.

EXAMPLE 5

1-[8-(N-Methylcarbamoyl)octyl]imidazole

To a suspension of 0.18 g of 63% sodium hydride (dispersed in mineral oil) in 30 ml of dry N,N-dimethylformamide was added 0.21 g of imidazole at room temperature and then the mixture was heated to 80° C.

A solution of 0.77 g of 8-(N-methylcarbamoyl)octylbromide in 2 ml of dry N,N-dimethylformamide was added slowly at 80° C., and then the reaction mixture was stirred at 80° C. for 1 hour.

After removal of N,N-dimethylformamide under reduced pressure, 50 ml of dichloromethane was added to the residue, washed with water, and dried over magnesium sulfate.

The solvent was evaporated and the residue was chromatographed on silica gel using dichloromethane-ethanol (20:1).

The eluate was recrystallized from chloroform-ether-n-hexane to give 0.18 g of 1-[8-(N-methylcarbamoyl)octyl]-imidazole as colorless crystals, (m.p. 64°–66° C.)

IR Absorption Spectrum (KBr)

νNH: 3325 cm$^{-1}$
νCH: 3100 cm$^{-1}$
νCO: 1640 cm$^{-1}$

NMR Spectrum (CDCl$_3$)

δ 1.1–1.9 (m, 12H), 2.08 (t, 2H), 2.67 (d, 3H), 3.83 (t, 2H), 6.25–6.70 (br, 1H), 6.81 (br-s, 1H), 6.92 (br-s, 1H), 7.35 (br-s, 1H)

$$N\underset{\diagdown=\diagup}{\overset{\diagup\frown\diagdown}{N}}N-(CH_2)_n-CN$$

| n | b.p. | Yield (%) | IR (neat) cm$^{-1}$ | NMR (CDCl$_3$): δ |
|---|---|---|---|---|
| 3 | 142–144° C. (0.5 mmHg) | 65 | ν CH: 3110 ν CN: 2250 | 1.95–2.45 (m, 4H), 4.11 (t, 2H), 6.89 (t, 1H), 7.02 (t, 1H), 7.44 (s, 1H) |
| 4 | 172–173° C. (2 mmHg) | 55 | ν CH: 3100 ν CN: 2240 | 1.5–2.2 (m, 4H), 2.38 (t, 2H), 4.02 (t, 2H), 6.91 (t, 1H), 7.04 (br-s, 1H), 7.46 (s, 1H) |
| 6 | 176–177° C. (0.5 mmHg) | 62 | ν CH: 3100 ν CN: 2240 | 1.1–2.0 (m, 8H), 2.33 (t, 2H), 3.94 (t, 2H), 6.85 (t, 1H), 7.00 (t, 1H), 7.40 (s, 1H) |
| 9 | — | 60 | ν CH: 3100 ν CN: 2240 |  |

Elemental Analysis

Calcd. for C$_{13}$H$_{23}$ON$_3$ (%): C, 65.78; H, 9.77; N, 17.71; Found (%): C, 65.52; H, 9.51; N, 17.41.

The following compounds can be prepared in a similar manner.

$$N\underset{\diagdown=\diagup}{\overset{\diagup\frown\diagdown}{N}}N-(CH_2)_n-CON\diagup_{R'}^{R}$$

| n | R | R' | b.p. or m.p. | IR: cm$^{-1}$ | NMR: δ |
|---|---|---|---|---|---|
| 3 | H | H | m.p. 102–103° C. (colorless prisms) | ν NH$_2$: 3320 ν CH: 3150 ν CO: 1690 | (DMSO-d$_6$) 1.8–2.2 (m, 4H), 3.95 (t, 2H), 6.84 (t, 1H), 6.75 (br, 1H), 7.09 (t, 1H), 7.28 (br, 1H), 7.55 (br-s, 1H) |

-continued $$\text{N} \underset{\underline{\qquad}}{\overset{\frown}{\diagup}} \text{N}-(CH_2)_n-CON\underset{R'}{\overset{R}{\diagup}}$$

| n | R | R' | b.p. or m.p. | IR: cm$^{-1}$ | NMR: δ |
|---|---|----|----|----|----|
| 6 | H | H | m.p. 114.5–116° C. (colorless needles) | ν NH$_2$: 3360<br>ν CH: 3140<br>ν CO: 1665 | (CDCl$_3$) 1.1–2.0 (m, 8H), 2.20 (t, 2H),<br>3.91 (t, 2H), 6.09 (br, 1H), 6.27 (br, 1H),<br>6.85 (t, 1H), 6.98 (t, 1H), 7.4 (br-s, 1H) |
| 6 | Et | Et | — (colorless oil) | ν CH: 3100<br>ν CO: 1635 | (CDCl$_3$) 1.0–2.0 (m, 14H), 2.28 (t, 2H),<br>3.30 (q, 2H), 3.38 (q, 2H), 3.93 (t, 2H),<br>6.88 (t, 1H), 7.02 (br-s, 1H), 7.44 (br-s, 1H) |
| 7 | H | H | m.p. 112–113° C. (colorless leaflets) | ν NH$_2$: 3380<br>ν CH: 3150<br>ν CO: 1665 | (DMSO-d$_6$) 1.1–1.85 (m, 10H), 2.04 (t, 2H),<br>3.93 (t, 2H), 6.62 (br, 1H), 6.83 (t, 1H),<br>7.08 (t, 1H), 7.15 (br, 1H), 7.55 (br-s, 1H) |

EXAMPLE 6

1-(7-Aminoheptyl)imidazole

A solution of 10.0 g of 1-(6-cyanohexyl)imidazole, which was prepared by the same procedure as described in Example 4, in 40 ml of concentrated hydrochloric acid and 100 ml of ethanol was hydrogenated over 1.5 g of platinum dioxide at room temperature under 4 atms.

After concentration under reduced pressure, 20 ml of 10% sodium hydroxide was added to the residual oil and the alkaline solution was extracted with dichloromethane and dried over magnesium sulfate.

The solvent was evaporated and the residual oil was distilled under vacuum (136°–137° C./0.5 mmHg) to give 8.0 g (78%) of 1-(7-aminoheptyl)imidazole as a colorless oil.

IR Absorption Spectrum (neat)

νNH$_2$: 3350 cm$^{-1}$

NMR Spectrum (CDCl$_3$)

δ1.18 (s, 2H), 1.2–1.9 (m, 10H), 2.66 (t, 2H), 3.91 (t, 2H), 6.85 (t, 1H), 6.99 (br-s, 1H), 7.40 (s, 1H)

Elemental Analysis

Calcd. for C$_{11}$H$_{19}$N$_3$ (%): C, 66.25; H, 10.57; N, 23.18; Found (%): C, 66.34; H, 10.81; N, 23.25.

EXAMPLE 7

1-(4-Aminobutyl)imidazole

In a similar manner as above, the catalytic hydrogenation of 16.0 g of 1-(3-cyanopropyl)imidazole, which was prepared by the same procedure as described in Example 4, gave 12.0 g of 1-(4-aminobutyl)imidazole as a colorless oil, b.p.: 108°–109° C./0.5 mmHg.

IR Absorption Spectrum (neat)

νNH$_2$: 3370 and 3290 cm$^{-1}$

NMR Spectrum (CDCl$_3$)

δ1.15 (br-s, 2H), 1.2–2.0 (m, 4H), 2.70 (t, 2H), 3.93 (t, 2H), 6.84 (t, 1H), 6.98 (br-s, 1H), 7.39 (s, 1H)

Elemental Analysis

Calcd. for C$_7$H$_{13}$N$_3$ (%): C, 60.40; H, 9.41; N, 30.19; Found (%): C, 60.59; H, 9.67; N, 29.92.

EXAMPLE 8

1-[7-(N,N-Diethylamino)heptyl]imidazole

To a suspension of 0.3 g of lithium aluminum hydride in 100 ml of dry tetrahydrofuran was added slowly 2.0 g of 1-[6-(N,N-diethylcarbamoyl)hexyl]imidazole, which was prepared by the same procedure as described in Example 5, in 10 ml of dry tetrahydrofuran at room temperature, and then the reaction mixture was refluxed for 5 hours.

After cooling, the reaction mixture was treated with 10% sodium hydroxide and filtered.

The filtrate was dried over magnesium sulfate and evaporated under reduced pressure.

The residual oil was chromatographed on silica gel using dichloromethane-ethanol (5:1) to give 0.26 g of 1-[7-(N,N-diethylamino)heptyl]imidazole as a colorless oil.

IR Absorption Spectrum (neat)

νCH: 3100 cm$^{-1}$

NMR Spectrum (CDCl$_3$)

δ0.95 (t, 6H), 1.1–1.9 (m, 10H), 2.36 (t, 2H), 2.48 (q, 4H), 3.88 (t, 2H), 6.83 (t, 1H), 6.99 (br-s, 1H), 7.39 (br-s, 1H)

Elemental Analysis

Calcd. for C$_{14}$H$_{27}$N$_3$ (%): C, 70.83; H, 11.47; N, 17.70; Found (%): C, 70.62; H, 11.31; N, 17.89.

REFERENCE EXAMPLE 1

Inhibitory Potency of Imidazole Compounds on Thromboxane Synthetase

Inhibitory potency of imidazole compounds on thromboxane synthetase was measured by a modification of the method of Moncada et al., (Prostaglandins, Vol. 13, 611, 1977).

(1-C$^{14}$)-Prostaglandin H$_2$, obtained by the enzymatic biosynthesis with ram seminal vesicle microsomes and (1-C$^{14}$)-arachidonic acid, was incubated with rabbit platelet microsomes containing 0.025 μM and 0.5 μM of the test compound at 24° C. for 1 minute. The termination of the reaction and the extraction of a radioactive materials were carried out by the addition of a mixture of ethyl acetate/methanol/0.2 M citric acid (30:4:1 by volume). The extracts were dried over anhydrous sodium sulfate and aliquots were analyzed by thin layer chromatography in a solvent of chloroform/ethyl acetate/methanol/acetic acid/water (70:30:8:0.5 by volume). A spot of thromboxane B$_2$ was counted by a packard Radiochromatogram Scanner.

The inhibitory potency of imidazole compounds is shown in the table below.

| Compound | Inhibition (%) | |
|---|---|---|
| | 0.025 μM | 0.5 μM |
| N-(6-methoxycarbonylhexyl)imidazole (known compound) | 5.5 | 25.7 |
| N-(6-carboxyhexyl)imidazole hydrochloride | 10.1 | 76.1 |
| N-(7-carboxyheptyl)imidazole hydrochloride | 31.2 | 89.0 |
| N-(8-carboxyoctyl)imidazole hydrochloride | 42.2 | 90.8 |
| N-(9-carboxynonyl)imidazole hydrochloride | 20.2 | 72.5 |
| N-(10-carboxydecyl)imidazole hydrochloride | 9.2 | 40.4 |
| N-(11-carboxyundecyl)imidazole hydrochloride | 13.8 | 46.8 |

REFERENCE EXAMPLE 2

Acute Toxicity

The median lethal dose (LD$_{50}$) of N-(7-carboxyheptyl)imidazole and N-(6-methoxycarbonylhexyl)imidazole (known compound) were determined in dd-stain male mice (7 weeks old) by intravenous administration. The LD$_{50}$ values were calculated according to the Behrens-Kärber method. The results of the test are shown below.

| N-(7-carboxyheptyl)imidazole | 560 mg/kg |
|---|---|
| N-(6-methoxycarbonylhexyl)imidazole (known compound) | 140 mg/kg |

FORMULATION EXAMPLE 1

10 g of N-(7-carboxyheptyl)imidazole were admixed with 30 g of lactose, 15 g of Indian corn starch, 30 g of hydroxymethylcellulose, 2 g of calcium carboxymethylcellulose and 1 g of calcium stearate. The mixture was kneaded and shaped into 1,000 tablets.

FORMULATION EXAMPLE 2

The tablets obtained in Formulation Example 1 were placed in a rotary coating tank and a 10% ethanolic solution of 1 g of polyvinylacetal diethylaminoacetate and 0.3 g of macrogol 6000 was added to the tablets and the mixture was stirred and dried.

FORMULATION EXAMPLE 3

5 g of N-(7-carboxyheptyl)imidazole and 10 g of chlorobutanol were dissolved in distilled water for injection to make the total amount 1,000 ml. 1 ml of the solution was poured into an ampoule to make 1,000 ampoules. The air was purged with nitrogen, and the ampoules were heated at 121° C. for 15 minutes to sterilize the solution to obtain an injectable preparation.

While the invention has been described in detail and with reference to specific embodiments thereof, it will be apparent to one skilled in the art that various changes and modifications can be made therein without departing from the spirit and scope thereof.

What is claimed is:

1. A compound of the formula:

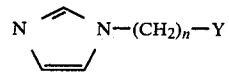

wherein Y is carboxyl, and n is an integer of 6 to 9 or a pharmaceutically acceptable salt thereof.

2. The compound of claim 1, wherein n is 6.
3. The compound of claim 1, wherein n is 7.
4. The compound of claim 1, wherein n is 8.
5. The compound of claim 1, wherein n is 9.
6. A pharmaceutical composition comprising a compound of claim 1 as an active ingredient in an amount effective for the treatment of a disease caused by thromboxane A$_2$ and a pharmaceutically acceptable carrier or diluent.
7. The pharmaceutical composition of claim 6 wherein the compound of claim 1 is present in an amount effective for the treatment of inflammation, hypertension, thrombus, cerebral apoplexy or asthma.
8. The pharmaceutical composition of claim 6 or 7 wherein said active ingredient is 1-(7-carboxyheptyl)imidazole.
9. A method for treating inflammation comprising administering a therapeutically effective amount of a compound of the formula:

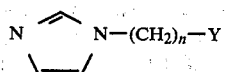

to a subject afflicted with the same, wherein Y is carboxyl, hydroxymethyl, N-di or -mono straight or branched chain C$_1$-C$_4$ alkyl substituted or unsubstituted carbamoyl, cyano or N-di or -mono straight or branched chain C$_1$-C$_4$ alkyl substituted or unsubstituted aminomethyl, and n is an integer of 3 to 20, or a pharmaceutically acceptable salt thereof.

10. A method for treating hypertension comprising administering a therapeutically effective amount of a compound of the formula:

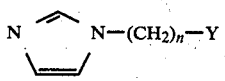

to a subject afflicted with the same, wherein Y is carboxyl, hydroxymethyl, N-di or -mono straight or branched chain C$_1$-C$_4$ alkyl substituted or unsubstituted carbamoyl, cyano or N-di or -mono straight or branched chain C$_1$-C$_4$ alkyl substituted or unsubstituted aminomethyl, and n is an integer of 3 to 20, or a pharmaceutically acceptable salt thereof.

11. A method for treating thrombus comprising administering a therapeutically effective amount of a compound of the formula:

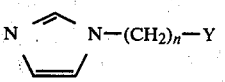

to a subject afflicted with the same, wherein Y is carboxyl, hydroxymethyl, N-di or -mono straight or branched chain C$_1$-C$_4$ alkyl substituted or unsubstituted carbamoyl, cyano or N-di or -mono straight or branched chain $C_1$-$C_4$ alkyl substituted or unsubstituted aminomethyl, and n is an integer of 3 to 20, or a pharmaceutically acceptable salt thereof.

12. A method for treating cerebral apoplexy comprising administering a therapeutically effective amount of a compound of the formula:

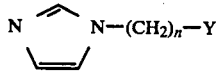

to a subject afflicted with the same, wherein Y is carboxyl, hydroxymethyl, N-di or -mono straight or branched chain $C_1$-$C_4$ alkyl substituted or unsubstituted carbamoyl, cyano or N-di or -mono straight or branched chain $C_1$-$C_4$ alkyl substituted or unsubstituted aminomethyl, and n is an integer of 3 to 20, or a pharmaceutically acceptable salt thereof.

13. A method for treating asthma comprising administering a therapeutically effective amount of a compound of the formula:

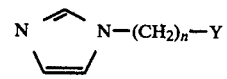

to a subject afflicted with the same, wherein Y is carboxyl, hydroxymethyl, N-di or -mono straight or branched chain $C_1$-$C_4$ alkyl substituted or unsubstituted carbamoyl, cyano or N-di or -mono straight or branched chain $C_1$-$C_4$ alkyl substituted or unsubstituted aminomethyl, and n is an integer of 3 to 20, or a pharmaceutically acceptable salt thereof.

14. The method of claim 9, 10, 11, 12 or 13 wherein said compound is 1-(7-carboxyheptyl)-imidazole.

* * * * *